US00PP15828P2

(12) United States Plant Patent
Kawashima

(10) Patent No.: US PP15,828 P2
(45) Date of Patent: Jul. 5, 2005

(54) ***OSTEOSPERMUM* PLANT NAMED 'KAKEGAWA AU13'**

(50) Latin Name: *Osteospermum hybrida*
Varietal Denomination: Kakegawa AU13

(75) Inventor: Moriya Kawashima, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 93 days.

(21) Appl. No.: 10/775,616

(22) Filed: Feb. 10, 2004

(51) Int. Cl.[7] ..... A01H 5/00
(52) U.S. Cl. ..... Plt./360
(58) Field of Search ..... Plt./360

(56) References Cited

PUBLICATIONS

Proven Winners: *Osteospermum* hybrids. Elsner pac Jungpflanzen GbR [online], [retrieved on Jun. 21, 2004]. Retrieved from the Internet <http://www.pac–elsner.com/uk/proven–winners/proven–index.htm>.*

* cited by examiner

*Primary Examiner*—Anne Marie Grunberg
*Assistant Examiner*—June Hwu
(74) *Attorney, Agent, or Firm*—Jondle & Associates P.C.

(57) ABSTRACT

An *Osteospermum* cultivar particularly distinguished by its orange flower color and tendency to hold flowers open later in the evening.

1 Drawing Sheet

Genus and species: *Osteospermum hybrida.*
Variety denomination: 'Kakegawa AU13'.

BACKGROUND OF THE NEW PLANT

The variety 'Kakegawa AU13' originated from a cross made in March 2001 in Misato, Japan. The female parent was a tetraploid *Osteospermum* sp. developed using the variety 'Seikilrem' (U.S. Plant Pat. No. 13,407). The male parent was an unnamed *Dimorphotheca sinuate* with small, orange flowers, shiny petals, long internodes and prostrate habit. Seed from this cross was sown in June 2001 and plants were transplanted to the outdoor field. In October 2001, single-plant selections were made for vegetative propagation using plant habit and flower color as selection criteria. One selection, designated breeder code M2-139, became the new variety 'Kakegawa AU13'. The variety 'Kakegawa AU13' was found to be stable and reproduce true to type in successive generations of asexual propagation.

DESCRIPTION OF PHOTOGRAPHS

This new *Osteospermum* plant is illustrated by the accompanying photographs which show blooms and foliage of the plant in full color. The colors shown are as true as can be reasonably obtained by conventional photographic procedures.

DESCRIPTION OF THE NEW CULTIVAR

Figure 1:
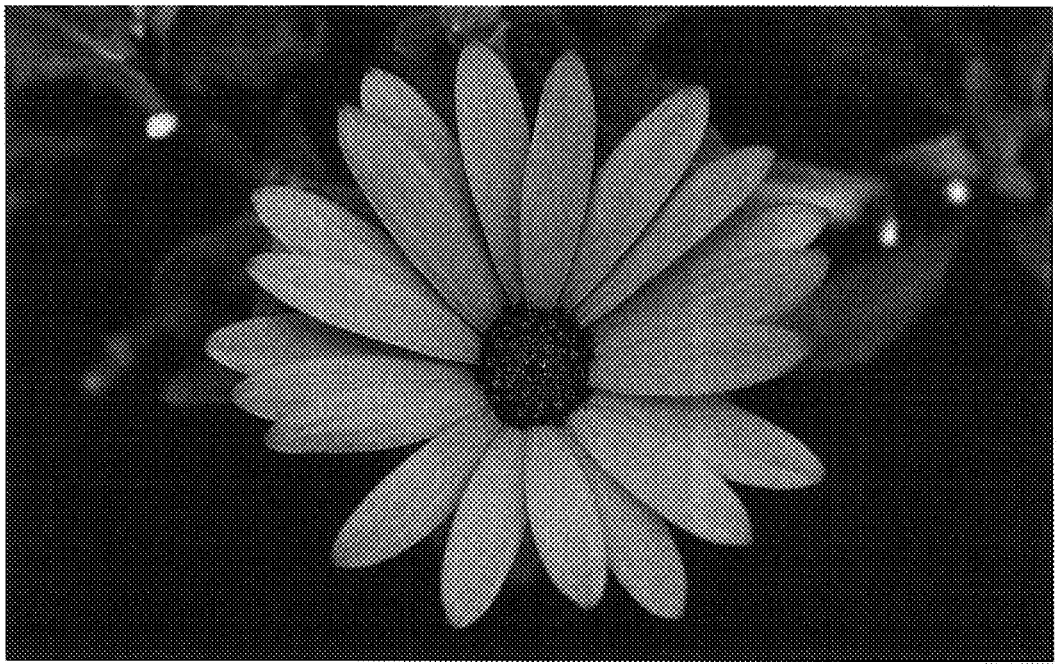
FIG. 1 shows a close-up view of a single inflorescence.
Figure 2:
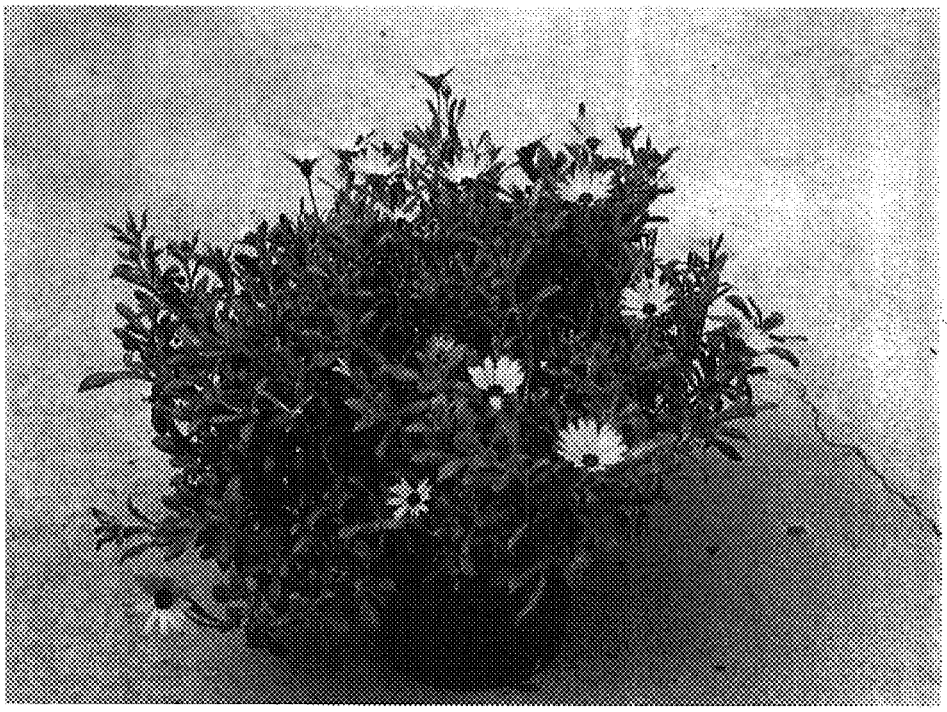
FIG. 2 shows a side view of the entire plant, including flower buds, open blooms and foliage.

The following detailed descriptions set forth the distinctive characteristics of 'Kakegawa AU13'. The data which defines these characteristics were collected from asexual reproductions carried out in Salinas, Calif. Data was collected on plants 20 weeks from transplanting rooted cuttings into 16 cm diameter pots, one plant per pot. Color references are to The R.H.S. Colour Chart of The Royal Horticultural Society of London (R.H.S.).

DESCRIPTION OF THE NEW PLANT

Classification:
- *Family.*—Compositae.
- *Botanical.—Osteospermum hybrida.*

Parentage:
- *Female parent.*—Breeding line 'Seikilrem' (U.S. Plant Pat. No. 13,407).
- *Male parent.*—Breeding line *Dimorphotheca sinuate* (unnamed).

Growth:
- *Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.
- *Environmental conditions for plant growth.*—Rooted cuttings are transplanted to pots with a 16 cm diameter, one plant per pot. Peat moss-based growing media is used. The pots are watered using a 150–200 ppm fertilizer solution containing 18% nitrogen, 8% phosphorus and 18% potassium. The soil is allowed to dry between waterings. During the first few weeks after transplanting the plants should have evening temperatures around 15–18° C. for good root growth. When plants reach 7.5–10 cm in height they are pinched back to 5–6 leaves to promote branching. Spring and summer daytime high temperatures in Salinas, Calif., where the data was collected, range from 16–25° C.
- *Time to bloom from propagation.*—Approximately four weeks when rooted vegetative cuttings are transferred to a 16 cm. diameter pot. Flowering season is all year in the United States. Vernalization is not required to induce flowering.

*Habit.*—Prostrate.
*Life cycle.*—Perennial.

Plant:
*Form.*—Low growing, open branching.
*Plant size.*—Height is 20–30 cm; width 50–75 cm.

Stems:
*Internode length.*—1.0–2.5 cm.
*Stem color.*—Yellow-green (RHS 144A).
*Stem description.*—Ancipital.
*Stem diameter.*—4.0–6.0 mm.
*Pubescence.*—Slight.
*Pubescence shape.*—Linear.
*Pubescence color.*—White (RHS N155A).

Leaves:
*Arrangement.*—Alternate.
*Shape.*—Oblanceolate.
*Apex.*—Mucronate.
*Base.*—Decurrent.
*Margin.*—Serrate.
*Venation.*—Pinnate.
*Surface.*—Dull, smooth.
*Surface pubescence.*—Slight, white (RHS N155A).
*Length.*—5.0–7.5 cm.
*Width.*—2.0–3.0 cm.
*Thickness.*—1.0 mm.
*Color.*—Upper is green (RHS 137A); Lower is green (RHS 137B).
*Venation color.*—Upper is green (RHS 138B); Lower is green (RHS 138B).

Inflorescence:
*Type.*—Capitulum (head); disc florets are perfect and ray florets are carpellate.
*Diameter.*—6.0–7.5 cm.
*Depth.*—2.5–3.5 cm.
*Petal numbers.*—18–22.
*Disc diameter.*—1.1–1.3 cm.
*Disc floret number.*—105–110.
*Flowering habit.*—Determinate.
*Flowers life span.*—3–4 days.
*Fragrance.*—None.
*Seed production.*—None.
*Peduncle length.*—2.5–5.0 cm.
*Peduncle diameter.*—2.0 mm.
*Peduncle color.*—Yellow-green (RHS 145A).
*Peduncle texture.*—Dull, slight pubescence.
*Phyllaries.*—18–22 per inflorescence, free, arranged symmetrically; Length — 1.1–1.4 cm; Width — 1.5–2.0 mm; Apex — Acute; Margin — Entire; Shape — Linear, acute; Color — Upper, yellow-green (RHS 144A); Lower, yellow-green (RHS 144A).
*Bud color.*—143A (green) at tip; 144B (yellow-green) at base; initial ray floret color is 25B (orange). Bud shape: Longitudinal cross-section is deltoid. Bud surface texture: Pubescent. Bud apex: Acute. Bud base: Truncate. Bud size: Length is 1.2–1.4 cm; Diameter is 0.9–1.1 cm.

Ray florets:
*Corolla.*—One petal per ray floret. Only the outer row of florets are the ray florets.
*Petals length.*—3.6–3.9 cm.
*Petal width.*—0.7–0.8 cm.
*Petal shape.*—Spatulate.
*Petal apex.*—Acute.
*Petal margin.*—Entire.
*Petal color.*—Upper, orange (RHS 25B) with base violet (RHS 88B); Lower, orange, (RHS 25B) with base greyed-green (RHS 195A).
*Petal pubescence.*—Glabrous.
*Ovary.*—Superior.
*Pistil form.*—One style with two stigma branches.
*Pistil length.*—0.7–1.1 cm.
*Stigma form.*—One style with two stigma branches.
*Stigma color.*—Blue (RHS 99A).
*Style color.*—White (RHS 155C).

Disc florets:
*Color.*—Purple (RHS 103A).
*Shape.*—Tubular.
*Apex.*—Rounded.
*Surface.*—Dull, pubescent.
*Size.*—Length 1.3–1.5 cm; width 1.0–1.3 mm.
*Ovary.*—Superior.
*Pistil form.*—One style with two stigma branches.
*Style color.*—White (RHS N155A).
*Stigma color.*—Blue (RHS 103A).
*Stamens.*—5, fused into a single tube.
*Anther color.*—Blue (RHS 99A).
*Pollen color.*—Orange (RHS 24A).

DISEASE AND INSECT RESISTANCE

Plants are susceptible to aphids, thrips, whiteflies and worms.

COMPARISON WITH KNOWN CULTIVARS

'Kakegawa AU13' is a distinct variety of *Osteospermum* owing to its prostrate-like habit; it grows low, stretches out, is not dense, does not contain multiple branching, and is open which makes it easy to see through portions of the plant. Its base color is more of a violet-blue, which is a darker color in contrast to the base on the comparison variety. The new cultivar is most similar to the variety 'Seikimora' (U.S. Plant Pat. No. 13,409); however, there are differences as shown in Table 1 below.

TABLE 1

| Trait | 'Kakegawa AU13' | 'Seikimora' |
|---|---|---|
| Petals | Petal color, orange (RHS 25B) with distinct shade of violet (RHS 88B) at the base | Orange (RHS 25B) petals with violet-blue (RHS N92D) at the base |
| Peduncle length | 2.5–5.0 cm | 4.5–7.0 cm |
| Pollen color | Orange (RHS 24A) | Orange (RHS 25C) |

I claim:

1. A new and distinct cultivar of *Osteospermum* plant as shown and described herein.

* * * * *